United States Patent [19]

Erdmann et al.

[11] 3,973,944

[45] Aug. 10, 1976

[54] PEST CONTROL AGENT

[75] Inventors: Dietrich Erdmann; Gerhart Schneider; Wolfgang Koch, all of Darmstadt, Germany

[73] Assignee: Merck Patent Gesellschaft mit beschrankter Haftung, Darmstadt, Germany

[22] Filed: Dec. 15, 1970

[21] Appl. No.: 98,442

[30] Foreign Application Priority Data

Dec. 27, 1969  Germany............................ 1965134

[52] U.S. Cl........................................ 71/88; 71/67; 71/92; 71/93; 71/113; 71/121; 260/343.6
[51] Int. Cl.².............................................. A01N 9/00
[58] Field of Search.................................... 71/67, 88

[56] References Cited

UNITED STATES PATENTS

| | | | |
|---|---|---|---|
| 3,004,041 | 10/1961 | Hennis | 71/88 X |
| 3,193,562 | 7/1965 | Speziale et al. | 71/88 |
| 3,239,538 | 3/1966 | Speziale et al. | 71/88 X |

*Primary Examiner*—Glennon H. Hollrah
*Attorney, Agent, or Firm*—Millen, Raptes & White

[57] ABSTRACT

3-Cyano-4-phenyl-5-dimethylaminomethylene-5H-furanone-(2) and compositions containing the same, are useful for controlling the growth of undesirable pest plant growth, e.g., algae, weeds and undesirable grasses, when applied to the locus to be protected.

9 Claims, No Drawings

PEST CONTROL AGENT

BACKGROUND OF THE INVENTION

This invention relates to a method for the control of undesirable plant growth, more specifically to the use of 3-cyano-4-phenyl-5-dimethylaminomethylene-5H-furanone-(2).

It is known that undesired plant growth, e.g., weeds, can be controlled very effectively by employing herbicides which prevent the formation of chlorophyll in the seedlings, thus causing the seedlings to starve after the endosperm contained in the seed is consumed. A known herbicide exhibiting this effect is 3-amino-1,2,4-triazole (amitrole). It has been found that the active compound of this invention is also herbicidally effective in this manner.

The active compound of this invention is superior both to amitrole and to other herbicidal agents which are used to regulate the growth of undesired plants by other means than the prevention of chlorophyll formation. This is particularly true with respect to the degree and range of effectiveness, compatibility with cultivated plants and the amount of active ingredient employed.

SUMMARY OF THE INVENTION

This invention relates to pest plant control agents, especially herbicidal and algicidal formulations, containing 3-cyano-4-phenyl-5-dimethylaminomethylene-5H-furanone-(2) in combination with a pesticidal adjuvant, e.g., a conventional carrier and/or additive, as the sole active ingredient or one of a combination of active ingredients.

This invention also relates to a method of pest plant control, especially herbicidal and algicidal control, employing a composition containing 3-cyano-4-phenyl-5-dimethylaminomethylene-5H-furanone-(2), alone or in combination with at least one additional known pest control agent.

DETAILED DISCUSSION

Undesirable plant life can be controlled very effectively with the known 3-cyano-4-phenyl-5-dimethylaminomethylene-5H-furanone-(2), a compound of the formula:

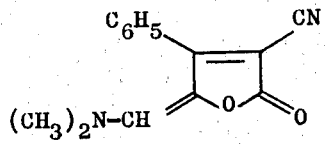

This compound is thus a valuable and effective agent for the control of pest plant growth. In particular, this compound exhibits excellent algicidal and herbicidal properties and according to a preferred embodiment of this invention, the active compound of this invention can also be advantageously employed in combination with other known herbicides.

The active compound of this invention, 3-cyano-4-phenyl-5-dimethylaminomethylene-5H-furanone-(2), is obtained in accordance with the process described in the Journal of Organic Chemistry, Volume 32 (1967), pp. 173 - 177.

The active compound of this invention and compositions containing it are valuable for controlling a wide variety of pest plants. Examples of the various types of undesirable plants which can be controlled with herbicidal formulations containing the active compound of this invention are: Agropyron, Agrostis, Alopecurus, Amaranthus, Apera, Avena, Bromus, Capsella, Carex, Centaurea, Chenopodium, Chrysanthemum, Cynodon, Cyperus, Digitaria, Echinochloa, Galeopsis, Galinsoga, Galium, Imperata, Lamium, Matricaria, Mentha, Mercurialis, Panicum, Papaver, Paspalum, Poa, Polygonum, Portulaca, Scirpus, Senecio, Setaria, Sinapis, Solanum, Sonchus, Sorghum, Stellaria and Urtica.

Examples of the types of algae which can be controlled with the active compound of this invention and compositions comprising them are Anacystis, Ankistrodesmus, Chlorella, Oscillatoria, Scenedesmus and Stichococcus.

A wide range of cultivated plants are tolerated by the active compound and compositions of this invention. Accordingly, growth of the above pest plants can be selectively controlled in cultivated areas containing a wide variety of desired plants. Examples of vegetation that are not seriously injured by the active compound and compositions containing the same at dose levels effective to control the growth of the above-described pest plants are: grain, e.g., rice (*Oryza sativa*), corn (Zea mays), wheat (*Triticum sativum*), barley (*Hordeum sativum*), oats (*Avena sativa*), rye (*Secale cereale*), millet (*Sorghum vulgare*); grass cultures; root crops and truck crops, e.g., common beets and sugar beets (*Beta vulgaris*), potatoes (*Solanum tuberosum*), cassava (*Manihot esculenta*), yams (*Dioscorea spec.*), sweet potatoes (*batatas, Impomoea batatas*); vegetables, e.g., onions (*Allium cepa*), lettuce (*Lactuca sativa*), tomatoes (*Lycopersicon esculentum*), celery (*Apium graveolens*), leek (*Allium porrum*), cucumber (*Cucumis sativus*), melons (*Cucumis melo*), cabbage types (*Brassica sp.*), asparagus (*Asparagus officinalis*), common and fine carrots (*Daucus carota*), spinach (*Spinacia oleracea*), eggplant (*aubergine, Solanum melongena*), konjak (*Amorphophallus conjac*); leguminous plants, e.g., soybeans (*Glycine soja*), peanuts (*Arachis hypogaea*), beans (*Phaseolus sp.*), broad bean (*Vicia faba*), peas (*Pisum sativum, Pisum arvense*), lentils (*Lens esculenta*), clover varieties (*Trifolium sp.*), alfalfa (*Medicago sativa*); oil plants, e.g., rape (*Brassica napus oleifera*), turnips (*Brassica rapa oleifera*), coconut palm (*Cocos nucifera*), oil palm (*Elaeis guineensis*), sunflower (*Helianthus annuus*), flax (*Linum usitatissimum*), olive (*Olea europaea*), sesame (*Sesamum indicum*); fruit cultures, such as apples (*Malus sp.*), pears (*Pyrus communis*), quince (*Cydonia oblonga*), cherry (*Prunus cerasus*), peach (*Prunus persica*), plum (*Prunus domesticus*), apricot (*Prunus armeniaca*), almond (*Prunus amygdalus*), strawberry (*Fragaria sp.*), currant (*Ribes sp.*), gooseberry (*Ribes grossularia*), raspberry (*Rubus idaeus*), blackberry (*Rubus fructicosus*), hazelnut (*Corylus avellana*), walnut (*Juglans regia*), citrus fruit (orange, tangerine, lemon, grapefruit; *Citrus sp.*), pineapple (*Ananascomosus*), banana (*Musa sp.*), avocado (*Persea americana*), mango (*Mangifera indica*), date (*Phoenix dactylifera*), fig (*Ficus carica sp.*), persimmon (*Diospyros kaki*), grape (*Vitis sp.*); fibrous plants, e.g., cotton (*Gossypium sp.*), flax (*Linum usitatissimum*), hemp (*Cannabis sativa*), jute (*Corchorus capsularis, Corchorus olitorius*), kapok (*Ceiba pentandra*), sisal (*Agave sp.*); decorative plants, e.g., roses (*Rosa sp.*), carnations (*Dianthus sp.*), cyclamen (*Cyclamen europaeum*), chrysanthemums (*Chrysanthemum* sp.), gladioli (*Gladiolus sp.*), tulips (*Tulipa sp.*), etc.; coffee (*Coffea arabica*), tea (*Thea sinensis*), cacao (*Theobroma cacao*), sugarcane (*Saccharum officinarum*), bamboo (*Bambusa sp.*), hop (*Humulus lupulus*), natural-rubber-yielding cultures, e.g., *Hevea brasiliensis, Manihot glaziovii, Taraxacum koksaghyz;* tobacco (*Nicotiana sp.*); as well as cultures of medicinal and spice plants, and groves of deciduous trees and conifers.

The compound and compositions of this invention are preferably employed in areas of rice cultivation. They are particularly valuable in this field of application because they satisfy the most important requirements of such agents, namely, high compatibility with the rice plants; effective combating of the water grass, which is the most frequently occurring undesired type of grass which grows in rice cultures; and a high algicidal or algistatic effect, which is of particular importance in rice growing, which takes place in flooded areas.

The active compound of this invention can be utilized in the form of the conventional formulations or compositions which are customarily used for plant protection agents and/or pest control agents. Thus, the active compound of this invention can be employed in the form of solid or liquid formulations with the addition of the conventional carrier vehicles, fillers and/or optional ingredients, e.g., spraying and/or dusting agents, solutions, dispersions, soluble powders, emulsifiable concentrates, granulated materials, or emulsions, which can, for example, also be sprayed as aerosols, etc.

The total amount of the active compound employed in these compositions is a herbicidally effective amount and generally ranges between about 1 and 95% by weight, and preferably between 5 and 80% by weight of the composition. When the active compound of this invention is employed in combination with at least another active pesticidal agent, the amount of the active compound of this invention present in the composition is generally between 0.5 and 90%, and preferably between 5 and 60% by weight.

The surface-active agent present in the preferred compositions of the invention is a wetting, dispersing or an emulsifying agent which will assist dispersion of the active compound therein. The surface-active agent can include such anionic, cationic and non-ionic agents as have heretofore been generally employed in pest control compositions. Suitable surface-active agents for use in compositions of this embodiment of the invention include detergents, e.g., sodium laurate; alkyl sulfates or alkyl sulfonates, such as sodium dodecyl sulfate or sulfonate; sulfonated and sulfated ethers; sulfonated alkyl-fatty acid esters, sulfonated glycol-fatty acid esters; quaternary ammonium salts, e.g., trimethylammonium iodide; amines and amides having longer aliphatic chains; monoethers of polyglycols with long-chained aliphatic alcohols, e.g., the reaction products of ethylene oxide or polyethylene glycol with higher aliphatic alcohols; monoesters of polyglycols with fatty acids, e.g., oleic acid; monoethers of polyglycols with alkylated phenols; partially esterified polyhydric alcohols, e.g., sorbitan trioleate; partially or entirely esterified polyglycol ethers of polyhydric alcohols, e.g., the tristearic acid ester of the polyglycol of sorbitan.

The compositions of this invention can also comprise a binder or suspending agent, such as, for example, cellulose and derivatives thereof, e.g., methyl-, ethyl-, hydroxypropyl-, or carboxymethylcellulose, tragacanth, pectins and gum arabic.

In general, the compositions of this invention contain up to 12% by weight of the surface-active agents, usually from 0.1 to 10% and preferably from 0.5 to 5% by weight of the composition.

The plant growth retardant compositions of this invention can contain, in addition to a surface active agent, finely divided inert solid carrier vehicles, e.g., bole, kaolin, siliceous chalk (naturally occurring mineral, consisting of kaolinite and quartz), bentonite, ground slate, pyrophyllite, talc, montmorillonite, chalk, dolomite, mica, silicic acid, aluminum or calcium silicate, kieselguhr or ground walnut hulls. Preferred diluents are hydrated silica, calcium silicate and bentonite. The amount of the finely divided inert solid diluent carrier vehicle can vary widely but will generally range from about 20 to 98% by weight and preferably between 35 and 95% by weight of the composition.

The compositions of the invention can also or alternatively contain a liquid inert diluent carrier vehicle or solvent, e.g., hydrocarbons, e.g., cyclohexane, xylene, solvent naphtha (aromatic hydrocarbon mixtures with boiling points of between 150° and 180° C.), petroleum, especially petroleum fractions with boiling points of between 80° and 200° C., tetrahydronaphthalene, decahydronaphthalene; aliphatic alcohols, e.g., methanol, ethanol, isopropanol, isobutanol, *n*-butanol, or hexanol; glycol ethers, e.g., 2-ethoxyethanol and 2-methoxyethanol; ketones, e.g., acetone, methyl ethyl ketone, diethyl ketone, methyl isobutyl ketone, isophorone, cyclohexanone, methylcyclohexanone, dioxane; dimethylformamide, N-methylpyrrolidone; dimethyl sulfoxide; and acetonitrile. Liquid carriers, when employed, are generally present in the compositions of the invention in an amount between about 15 and 98%, preferably about 30 to 90% by weight of the composition.

Mixtures of the above-mentioned solvents can also be employed in the practice of this invention. When emulsion concentrates are marketed as such, they are diluted in the usual manner with water prior to use. When the compositions or formulations employed contain one or more active compounds soluble in water, it is, of course, also possible to utilize water as the emulsifier or diluent for producing the emulsion concentrate.

According to another embodiment of this invention, the active compound can also be admixed with other chemicals which are used in agronomic and horticultural management and are compatible with the active compound of this invention. Such compounds may be, but are not restricted to, the classes of chemicals commonly known as herbicides, growth regulators or morpho-regulators and algicides. Best results are obtained when the active compound of this invention is used in combination with at least one halofatty acid derivative, e.g., sodium trichloroacetate and sodium 2,2-dichloropropionate.

Other optional ingredients which may be incorporated into the compositions of this invention include adhesion-promoting (i.e., binding) and evaporation-retarding agents, e.g., paraffin oils and glycerin.

The active compound and compositions of this invention can be applied directly or indirectly to the soil or plant as a pre-germination or post-germination treatment to the locus of the undesired plant growth. This can be achieved by means of: atomizing, spraying, pouring, strewing, dusting, rubbing, powdering, injection, infiltration, or soaking of plants or plant parts, such as tubers, bulbs, or seeds, as well as by incorporation into the culture substrate or soil.

By "locus" it is meant the pest plant itself, when it is visible above the ground or the immediate area of soil where the pest plant is developing or will otherwise develop.

The germination or growth of weeds and undesired grasses can normally be prevented by applying to the soil, in the pre-germination process, a herbicidal amount which is generally in an amount between about 0.45–90 lbs./acre, preferably about 0.9–18 lbs./acre (0.5–100, preferably 1–20 kg. per hectare) of the active compound of this invention, in the form of compositions containing said active compound as the sole active agent or in combination with other active pesticidal agents, e.g., herbicides. These amounts are tolerated by cultivated plants, for example, rice, corn, cotton, soybeans and potatoes. Thus, it is possible to combat various undesired grasses *Echinochloa crus-galli* (water grass or barnyard grass), *Digitaria spp.*, *Setaria spp.*, and *Sorghum spp.*, normally present during the cultivation of rice, corn and grain employing the active compound and compositions of this invention. By employing the active compound of the present invention either on top of the soil or in admixture with the soil, the undesired grasses can be controlled before they start to grow, without harming the seeded or already germinated or planted crops.

When utilized in the post-germination process by application to the plant growth, the agents of this invention inhibit the further development of many weeds, particularly in their early stages of development. In this manner, the application of the active compound of this invention, either alone or in the form of a composition, will prevent the further development of weeds and undesired grasses. When employed at minimum effective levels, there is no perceptible injury to crop plants including, e.g., sugar beets and common beets, carrots, cabbage, rape, peas, tomatoes, tobacco, black salsify, lettuce, cucumbers, melons, peanuts and permanent plants, e.g., fruit orchards, vineyards, strawberry cultures and asparagus plants.

The active compound of this invention is applied to the locus of the undesired vegetation or weeds in a herbicidal amount, that is, an amount sufficient to inhibit or retard the growth of the undesired vegetation. The exact amount which should be applied for optimum results depends on the desired effect, climatic conditions and the type and character of the plants to be treated and can readily be determined by those skilled in the art.

The effectiveness of the active compound of this invention was determined in the following experiments:

EXPERIMENT 1

Pre-germination treatment of previously sowed seeds of oats (*Avena sativa*), water grass (*Echinochloa crus-galli*), cucumber (*Cucumis sativus*) and radish (*Raphanus sativus*):

a. Method

Ten seeds were sown in compost-filled paper cups having a surface area of 50 cm$^2$ and each covered with 1 cm. of sand. On the next day, 25 ml. of an aqueous dilution of variously concentrated preparations of the active compound of this invention were poured thereon, respectively. Due to the high amount of water (25 ml./50 cm$^2$ corresponding to 50,000 l./hectare), the effective agent was flushed into the soil. After three weeks, the growth and condition of the young plants were evaluated.

b. Results

The minimum amount of the active compound (in kg./ha.) which prevented the germination of the seeds or caused the withering of all seedlings is set forth in Table 1, below. For comparison purposes, the table also contains the values found with the conventional herbicide amitrole.

TABLE 1

| Effective Agent | Preventing the Germination of the Seeds or Effecting the Withering of the Seedlings (kg./ha.) | | | |
|---|---|---|---|---|
| | Avena | Echinochloa | Cucumis | Raphanus |
| 3-cyano-4-phenyl-5-dimethylamino-methylene-5H-furanone-(2) | 2–3* | 2 | 2 | 1 |
| Amitrole | 5–10 | 3–4 | 10–20 | 5–10 |

*1.8 – 2.7 lbs./acre

The table demonstrates that the active compound of this invention, i.e., 3-cyano-4-phenyl-5-dimethylaminomethylene-5H-furanone-(2), is effective already in markedly smaller quantities than the comparison compound, amitrole.

EXPERIMENT 2

Selective extermination of weeds or undesired grasses in cultivated plant crops after spraying onto the soil a. Method

The cultivated crops (corn, cotton, soybean) and the weed grass seeds and weed seeds [water grass (*Echinochloa crus-galli*), amaranth (*Amaranthus spec.*), chickweed (*Stellaria media*)] were introduced into the culturing tanks one day prior to spraying. The seeds of the cultivated plants were sown in rows at a depth of 3 cm.; the seeds of the weed grasses and the weeds were sown at random in the upper layer of the soil at a thickness of 1 cm. The active agents were then sprayed onto the soil in different concentrated aqueous dilutions (approximately 1000 l./ha.). Conventional herbicidally effective agents trifluralin (2,6-dinitro-4-trifluoromethyl-N,N-di-*n*-propyl-aniline) and atrazine (2-chloro-4-ethylamino-6-isopropylamino-1,3,5-triazine) were employed in comparison experiments. The evaluation was conducted three weeks after spraying.

b. Results

1. Combating of the Weeds and Undesired Grasses

In Table 2, column A contains the active agents employed, column B the quantities utilized (kg./ha.), and columns C, D and E, contain the results produced with the weeds and undesired grasses under consideration.

The following code is the basis for the numerical evaluation data set forth in the table:

| Rating | Weed Extermination in Percent |
|---|---|
| 1 | 100 (very good) |
| 2 | |
| 3 | 95 (good) |
| 4 | |
| 5 | 85 (satisfactory) |
| 6 | |
| 7 | 65 (inadequate [unsatisfactory]) |
| 8 | |

| Rating | -continued<br>Weed Extermination in Percent |
| --- | --- |
| 9 | 0 (none [totally ineffective]) |

TABLE 2

| A<br>Effective<br>Agent | B<br>Amount<br>Employed<br>(kg./ha.) | C<br>Echino-<br>chloa | D<br>Amaranthus | E<br>Stellaria |
| --- | --- | --- | --- | --- |
| 3-Cyano-4-phenyl-5-di-methylamino-methylene-5H-furanone-(2) | 4 | 5 | 1 | 3 |
|  | 6 | 3 | 1 | 1 |
| Trifluralin | 4 | 4 | 3 | 8 |
|  | 6 | 3 | 3 | 7–8 |
| Atrazine | 4 | 9 | 1 | 3 |

The comparative experimental data in Table 2 clearly demonstrate that the active compound of this invention exhibits a greater range of effectiveness than the comparison compounds.

2. Compatibility with Respect to Corn, Cotton and Soybean

TABLE 3

| Effective Agent | Amount Employed (kg./ha.) | Corn | Cotton | Soybean |
| --- | --- | --- | --- | --- |
| 3-Cyano-4-phenyl-5-dimethylamino-methylene-5H-furanone-(2) | 6 | good | good | good |
| Trifluralin | 6 | incompatible | good | good |
| Atrazine | 4 | good | incompatible | incompatible |

It can be seen from this table that the active compound of this invention exhibits a wider range of compatibility for various cultivated plants than the comparison compounds.

EXPERIMENT 3

A. Combating Water Grass (*Echinochloa crus-galli*) in Cultures of Planted Rice (*Oryza sativa*)

Soil mixed to a depth of 4 cm. with seeds of water grass was filled into experimental vessels and flooded with water to a level of 1.5 cm. On the following day, rice plants in the 2–3 leaf stage were planted. Seven days thereafter, the formulations containing the active compounds of this invention were sprayed or strewed into the irrigation water. The evaluation with respect to the effect on the weed and the compatibility with rice was carried out four weeks after applying the effective agents. Experiments were conducted with a halo-fatty acid derivative, sodium trichloroacetate, which has been frequently employed for combating weeds in rice cultures heretofore. Comparative data was obtained when the sodium trichloroacetate was used alone or in combination with the active compound of this invention. The results are compiled in Table 4, below. The rating numbers with respect to the water grass are based on the code set forth in connection with Table 2; the rating numbers in connection with rice compatibility were obtained in accordance with the following code:

| Rating Number | Phytotoxic Damage |
| --- | --- |
| 1 | none |
| 2 |  |
| 3 | minor |
| 4 |  |
| 5 | moderate |
| 6 |  |
| 7 | very strong |
| 8 |  |
| 9 | total |

Accordingly, the smaller the two rating numbers, or the sum of said numbers, the greater the usefulness of the tested compound as a herbicidal agent.

TABLE 4

| Effective Agent | Amount Employed (kg./ha.) | Formulation and Content of Effective Agent | Effect on Water Grass | Rice Compat-ibility | Sum of Rating Numbers |
| --- | --- | --- | --- | --- | --- |
| 3-Cyano-4-phenyl-5-di-methylamino-methylene-5H-furanone-(2) | 1.5 | Sprayable Powder, 50% | 5 | 3 | 8 |
|  | 3.0 | 50% | 3 | 3–4 | 6–7 |
|  | 4.5 | 50% | 2 | 4 | 6 |
|  | 3.0 | Aqueous Dispersion, 25% | 2–3 | 3–4 | 5–7 |
|  | 1.5 | Granules, 6% | 5–6 | 2–3 | 7–9 |
|  | 3.0 | 6% | 3 | 3 | 6 |
|  | 4.5 | 6% | 2–3 | 3–4 | 5–7 |
| Sodium Tri-chloro-acetate | 3.0 | Granules, 12% | 6 | 3 | 9 |
|  | 6.0 | 12% | 5 | 4 | 9 |
|  | 9.0 | 12% | 4 | 8 | 12 |

TABLE 4-continued

| Effective Agent | Amount Employed (kg./ha.) | Formulation and Content of Effective Agent | Effect on Water Grass | Rice Compat- ibility | Sum of Rating Numbers |
| --- | --- | --- | --- | --- | --- |
| 3-Cyano-4-phenyl-5-di-methylamino-methylene-5H-furanone-(2) and Sodium Trichloroacetate | 1.5 + 3.0 | Granules, 6% + Granules, 12% | 4 | 3 | 7 |
|  | 1.5 + 6.0 | 12% | 3–4 | 4 | 7–8 |
|  | 3.0 + 3.0 | 12% | 2 | 3–4 | 5–6 |
|  | 3.0 + 6.0 | 12% | 1 | 4–5 | 5–6 |

The results compiled in Table 4 demonstrate that the active compound of this invention is more suitable for the selective control and combating of water grass in rice than the halo-fatty acid derivative, sodium trichloroacetate. Similar results were also obtained with the commercial preparation dalapon (sodium 2,2-dichloropropionate) in comparison experiments. Moreover, the results obtained with the combinations of the active compound of this invention and sodium trichloroacetate showed that the combined active agents exhibit a synergistic effect.

Similar results to those set forth in Table 4 were also achieved by employing the agents of this invention immediately after the planting of the rice plants.

B. Combating Water Grass (*Echinochloa crus-galli*) in Seeded Rice Cultures (*Oryza sativa*)

Seeds of water grass were mixed into the soil to a depth of 4 cm.; thereafter, rice was sown at a depth of 1 cm. After germination of the rice, the culture was flooded to a level of 1 cm. The herbicidal agents to be tested were applied either by spraying directly after sowing the rice (in case of using sprayable powder formulations or aqueous dispersions) or by spreading the agents after the germination of the rice (when employing granular formulations). Four weeks after application of the agents, the effect of the agents on the water grass and on the rice was evaluated. The results are compiled in Table 5, below. The numerical ratings are based on the evaluation codes described in connection with Tables 2 and 4.

TABLE 5

| Effective Agent | Amount Employed (kg./ha.) | Formulation and Content of Effective Agent | Effect on Water Grass | Rice Compat- ibility | Sum of Rating Numbers |
| --- | --- | --- | --- | --- | --- |
| 3-Cyano-4-phenyl-5-di-methylamino-methylene-5H-furanone-(2) | 1.5 | Sprayable Powder, 50% | 3–4 | 1–2 | 4–6 |
|  | 3.0 | 50% | 2–3 | 2 | 4–5 |
|  | 4.5 | 50% | 2 | 4 | 6 |
|  | 3.0 | Aqueous Dispersion, 25% | 2–3 | 2–3 | 4–6 |
|  | 1.5 | Granules, 6% | 4 | 2 | 6 |
|  | 3.0 | 6% | 3 | 2–3 | 5–6 |
|  | 4.5 | 6% | 2–3 | 5 | 7–8 |
| Sodium Tri-chloro-acetate | 3.0 | Granules, 12% | 9 | 2–3 | 11–12 |
|  | 6.0 | 12% | 8 | 3–4 | 11–12 |
|  | 9.0 | 12% | 5 | 7–8 | 12–13 |
| 3-Cyano-4-phenyl-5-di-methylamino-methylene-5H-furanone-(2) and Sodium trichloroacetate | 1.5 + 3.0 | Granules, 6% + Granules, 12% | 3 | 2 | 5 |
|  | 1.5 + 6.0 | 12% | 2–3 | 4 | 6–7 |
|  | 3.0 + 3.0 | 12% | 1–2 | 2–3 | 3–5 |
|  | 3.0 + 6.0 | 12% | 1 | 4–5 | 5–6 |

This table likewise demonstrates that the active compound of this invention, when employed in the selective combating of water grass in rice, exhibits substantial advantages over sodium trichloroacetate, a typical halo-fatty acid derivative. Results similar to the above were also obtained in connection with other application and irrigation methods. Once again, a synergism between the active compound of the invention and sodium trichloroacetate is observed. This synergistic effect could also be verified in combinations with other halo-fatty acid derivatives, such as dalapon (sodium 2,2-dichloropropionate).

EXPERIMENT 4

Test for Algicidal Effect 20 ml. of a sterilized nutrient solution prepared by dissolving 1.0 g. of calcium nitrate, 0.25 g. of magnesium sulfate heptahydrate, 0.25 g. of potassium dihydrogen phosphate, 0.25 g. of potassium nitrate, and 20 mg. of iron sulfate in 3 liters of water, was mixed, in an Erlenmeyer flask, with 0.2 ml. of acetonic solution of the active agent of this invention (dilution series) and thereafter inoculated with a slurry of about $10^6$ cells of Chlorella pyrenoidosa in 1 ml. of water. Subsequently, the flasks were shaken for 7 days at 22° C. and under daylight and access of air on a vibrating table at 80 motions per minute. Thereafter, the number of alga cells were determined by counting. In Table 6 below, the concentrations of the active agents tested are set forth (in p.p.m. = parts per million) which effectively inhibit the reproduction of the algae. Substances compared included copper sulfate pentahydrate, a commercial algicide containing as the active agent a quaternary ammonium compound ("Dimanin" A, produced by Farbenfabriken Bayer), and triphenyltin acetate.

Table 6

| Effective Agent | Minimum Inhibitory Concentration With Respect to Chlorella (in p.p.m.) |
| --- | --- |
| 3-Cyano-4-phenyl-5-dimethylaminomethylene-5H-furanone-(2) | 2 |
| $CuSO_4 . 5 H_2O$ | 5 |
| "Dimanin" A | 5 |
| Triphenyltin Acetate | 3 |

This table demonstrates that the active compound of this invention is effective at a substantially lower concentration than the conventional algicidally effective agents examined herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

FORMULATION EXAMPLES

EXAMPLE 1
Sprayable Powder
- 25% 3-Cyano-4-phenyl-5-dimethylaminomethylene-5H-furanone-(2)
- 1% Sodium dialkyl naphthalene sulfonate
- 12% Hydrated silica
- 15% Sulfite waste liquor powder
- 47% Bole

EXAMPLE 2
Sprayable Powder
- 10% 3-Cyano-4-phenyl-5-dimethylaminomethylene-5H-furanone-(2)
- 30% 2-Ethylhexyl-2,4-dichlorophenoxyacetate
- 8% Oleic acid N-methyltauride
- 52% Hydrated silica

EXAMPLE 3
Sprayable Powder
- 15% 3-Cyano-4-phenyl-5-dimethylaminomethylene-5H-furanone-(2)
- 30% Sodium trichloroacetate
- 1% Sodium alkylbenzenesulfonate
- 3% Sulfite waste liquor powder
- 10% Precipitated aluminum silicate
- 41% Siliceous chalk (natural mixture of fine quartz and kaolin)

EXAMPLE 4
Sprayable Powder
- 40% 3-Cyano-4-phenyl-5-dimethylaminomethylene-5H-furanone-(2)
- 0.5% Sodium dialkyl naphthalene sulfonate
- 12% Sulfite waste liquor powder
- 25% Precipitated calcium silicate
- 22.5% Kaolin

EXAMPLE 5
Sprayable Powder
- 50% 3-Cyano-4-phenyl-5-dimethylaminomethylene-5H-furanone-(2)
- 1% Sodium alkyl sulfate
- 5% Nonylphenol polyglycol ether
- 10% Precipitated calcium silicate
- 34% Bole

EXAMPLE 6
Dispersion
- 25% 3-Cyano-4-phenyl-5-dimethylaminomethylene-5H-furanone-(2)
- 1% Carboxymethylcellulose
- 2% Alkylphenol polyglycol ether
- 1% Bentonite
- 71% Water

EXAMPLE 7
Dusting Agent
- 20% 3-Cyano-4-phenyl-5-dimethylaminomethylene-5H-furanone-(2)
- 10% Calcium silicate
- 2% Colophony
- 68% Bole

EXAMPLE 8
Granulated Composition
- 6% 3-Cyano-4-phenyl-5-dimethylaminomethylene-5H-furanone-(2)
- 2% Sulfite waste liquor powder
- 1% Sodium dialkyl naphthalene sulfonate
- 91% Arenaceous quartz (grain size 0.8 – 1.5 mm.)

EXAMPLE 9
Granulated Composition
- 12% 3-Cyano-4-phenyl-5-dimethylaminomethylene-5H-furanone-(2)
- 81% Bentonite
- 2% Sodium alkylbenzenesulfonate
- 5% Sulfite waste liquor powder

EXAMPLE 10
Granulated Composition
- 6% 3-Cyano-4-phenyl-5-dimethylaminomethylene-5H-furanone-(2)
- 12% Sodium trichloroacetate
- 77% Precipitated calcium silicate
- 2% Sodium alkyl sulfate
- 3% Sulfite waste liquor powder

EXAMPLE 11
Granulated Composition
- 10% 3-Cyano-4-phenyl-5-dimethylaminomethylene-5H-furanone-(2)
- 20% Sodium 2,2-dichloropropionate
- 10% Hydrated silica
- 3% Sodium carboxymethylcellulose
- 57% Calcium sulfate hemihydrate ($CaSO_4 . ½ H_2O$)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A composition for controlling undesired plant growth comprising, as an active ingredient a herbicidal effective amount of 3-cyano-4-phenyl-5-dimethylaminomethylene-5H-furanone-(2) in admixture with a finely divided inert insoluble solid carrier vehicle.

2. A composition according to claim 1 wherein the 3-cyano-4-phenyl-5-dimethylaminomethylene-5H-furanone-(2) is present in an amount between 5 and 80% by weight.

3. A composition according to claim 1 wherein said inert solid carrier is present in an amount from 20 to 98% by weight and is selected from the group consisting of hydrated silica, calcium silicate and bentonite.

4. A composition according to claim 1 further comprising a wetting, dispersing or emulsifying agent.

5. A method for controlling undesired plant growth which comprises applying to the locus to be protected a herbicidal effective amount of 3-cyano-4-phenyl-5-dimethylaminomethylene-5H-furanone-(2).

6. A method according to claim 5 wherein 3-cyano-4-phenyl-5-dimethylaminomethylene-5H-furanone-(2) is applied to soil at the rate of about 0.45 to 90 lbs./acre.

7. A method according to claim 6 wherein the rate of application to the soil is about 0.9 to 18 lbs./acre.

8. A method according to claim 5 wherein the 3-cyano-4-phenyl-5-dimethylaminomethylene-5H-furanone-(2) is applied to an area under rice cultivation.

9. A method according to claim 8 wherein the 3-cyano-4-phenyl-5-dimethylaminomethylene-5H-furanone-(2) is applied prior to the emergence of undesired grasses.

* * * * *